United States Patent [19]

Gerding

[11] 4,019,793

[45] Apr. 26, 1977

[54] PHARMACEUTICAL DOSAGE DISTRIBUTION APPARATUS

[76] Inventor: Paul W. Gerding, 7505 Kilbourn Drive, Fort Wayne, Ind. 46809

[22] Filed: Mar. 14, 1975

[21] Appl. No.: 558,320

[52] U.S. Cl. ................................ 312/209; 312/250

[51] Int. Cl.[2] .................. A47B 81/00; A61B 19/02; B01L 9/02; A47B 91/00

[58] Field of Search ............ 312/209, 234.1, 234.5, 312/244, 250, 257 SK, 257 SM, 311

[56] References Cited

UNITED STATES PATENTS

| | | | |
|---|---|---|---|
| 362,200 | 5/1887 | Campbell | 312/311 |
| 800,699 | 10/1905 | Wetherhead | 312/311 |
| 1,036,066 | 8/1912 | Bown | 312/311 |
| 1,487,856 | 3/1924 | Hauserman et al. | 312/257 SK |
| 2,575,661 | 11/1951 | Hickey | 312/209 |
| 2,758,387 | 8/1956 | Stann | 312/311 |
| 2,823,972 | 2/1958 | Saunders | 312/311 |
| 3,512,858 | 5/1970 | Relyea | 312/234.5 |
| 3,759,597 | 9/1973 | Johnston | 312/234.5 |
| 3,834,778 | 9/1974 | Morrison et al. | 312/209 |
| 3,846,004 | 11/1974 | Relyea | 312/209 |
| 3,876,268 | 4/1975 | Colver | 312/209 |

FOREIGN PATENTS OR APPLICATIONS

| | | | |
|---|---|---|---|
| 1,308,489 | 9/1962 | France | 312/234.1 |
| 706,601 | 3/1954 | United Kingdom | 312/311 |
| 934,324 | 8/1963 | United Kingdom | 312/209 |

*Primary Examiner*—Paul R. Gilliam
*Assistant Examiner*—V. N. Sakran

[57] ABSTRACT

A pharmaceutical dosage distribution apparatus having at least one enclosure which includes an opening in one side thereof, a door for closing the opening and having thereon locking means for locking the door in its closed position. A plurality of trays are provided, each tray including a plurality of compartments for receiving a predetermined single dosage of medication. Means are associated with each of the compartments for identifying the recipient of each dosage. Rack means are provided in the enclosure for removably receiving the trays. A wheeled cart including frame means slidably receives the enclosures and includes locking means for securing the enclosure in its received position in the frame.

6 Claims, 16 Drawing Figures

FIG-2
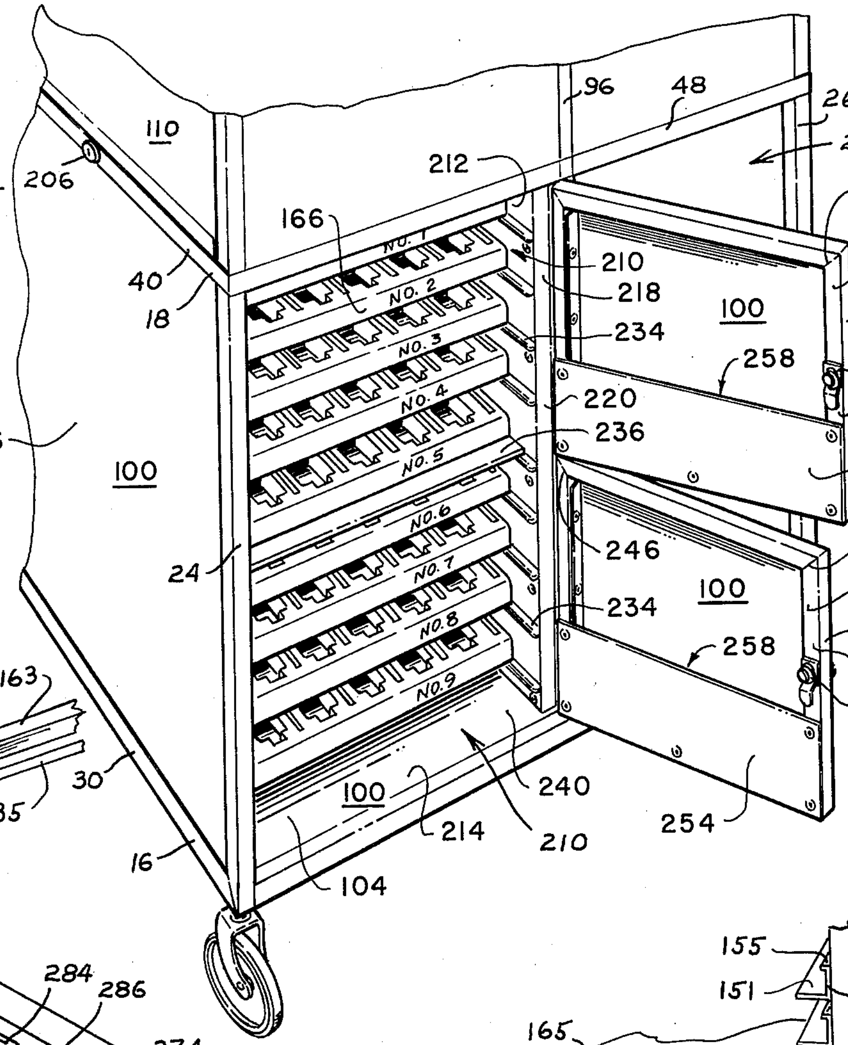
FIG-8b
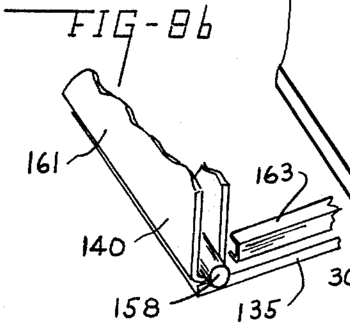
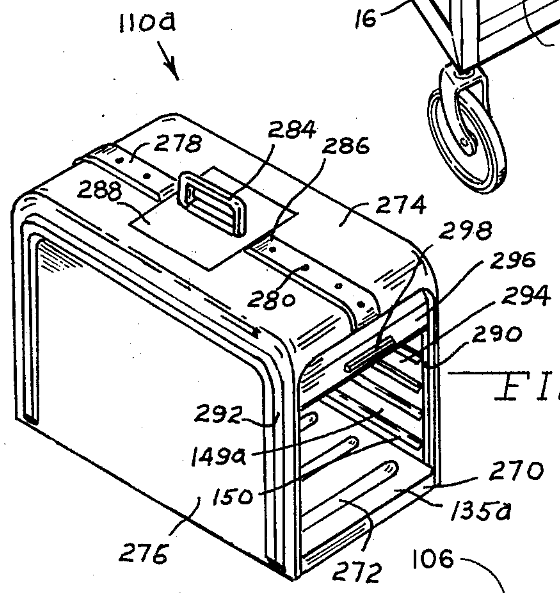
FIG-9
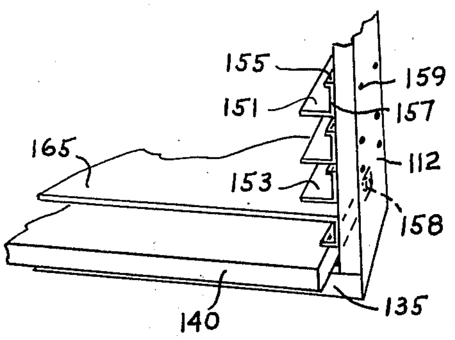
FIG-8c
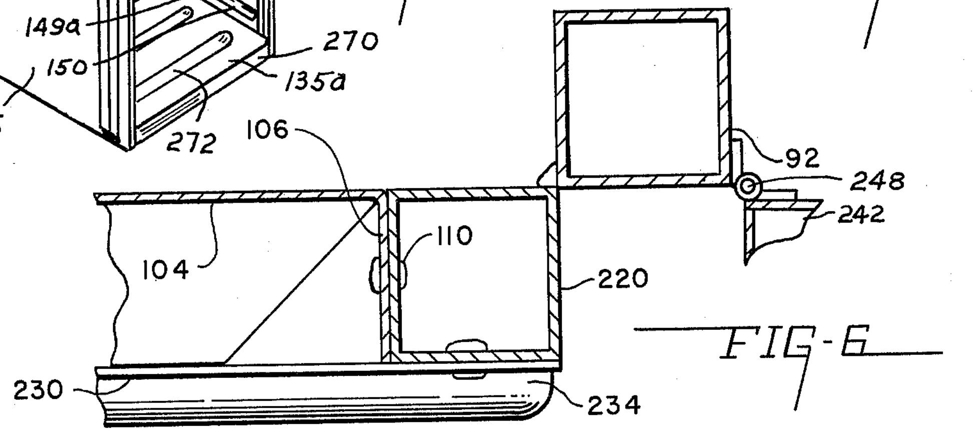
FIG-6

PHARMACEUTICAL DOSAGE DISTRIBUTION APPARATUS

BACKGROUND OF THE INVENTION

1. Field of the Invention

The present invention relates to devices for the preparation and distribution of pharmaceutical and related items at hospitals, nursing homes and the like and in particular to structures for packaging, organizing, transporting, and distributing such materials with improved efficiency, accuracy and convenience.

2. DESCRIPTION OF THE PRIOR ART

Conventionally, pharmaceuticals including prescription drugs and non-prescription drugs such as antipyretics, analgesics, and the like are prepared and distributed in large institutional facilities such as hospitals and nursing homes in a manner closely analogous to the dispensing of such drugs and medicines in the home.

The prescription and the non-prescription medicines for each patient in the institution are prepared and stored in prescription quantities. The individual dosages of the medicines are measured from the prescription quantities at or near the time of distribution thereof. This method of distributing medicine requires the institution to keep large inventories of medicine on hand, is time consuming for nurses and other professional people having the responsibility for preparing the individual dosages, and relies heavily upon the skills of these persons to insure that the dosages are accurate and properly distributed.

A significant improvement in this method of distributing medicine has been effected by the use of a system of prepackaging individual dosages of medicine in special trays. The medicine is prepared at a pharmacy, frequently remote from the institution. The trays or packaging devices are provided with a multiplicity of receptacles or compartments with the medicines being placed in the compartments in individual dosages according to a predetermined scheme such as, for example, sequentially according to room number. The trays are then transported to the institution and placed in special carts for transport to the individual patients. Such a system is described in U.S. Pat. No. 3,512,858, issued to Relyea. The system disclosed in the Relyea Patent, however, requires that a large and relatively bulky cart be continuously transported between a pharmaceutical preparation facility and the institution. Further, this last mentioned system requires a separate cart for each floor or area to be served and does not provide any means for transporting or otherwise distributing non-prescription materials that are typically stored in bulk quantities at a hospital. Substantial redundancy in equipment is also required inasmuch as one set of carts will typically be situated at the pharmaceutical preparation location while another set of carts is being used at the institution.

There exists, therefore, a need for an apparatus for preparing, organizing, transporting and distributing individual dosages of medicine and the like materials which eliminates unnecessary redundancy of the equipment. Such a system further requires minimization of the portions thereof that must be transported both for economy of transportation and initial expense of the equipment.

SUMMARY OF THE INVENTION

Broadly, the invention is a pharmaceutical dosage distribution apparatus which includes at least one manually transportatable enclosure. The enclosure includes means for slidably receiving therein a plurality of trays, each of the trays including a plurality of compartments for receiving a predetermined single dosage of medication. Means are associated with each of the compartments of the trays for identifying the recipient of the dosage. The apparatus further includes a wheeled cart including frame means for slidably receiving the enclosure therein.

It is therefore the object of the invention to provide an improved apparatus for the preparation, organizing, transporting and distribution of pharmaceuticals.

It is another object of the invention to provide such an apparatus which enables the efficient preparation and distribution of single dosage quantities of medicine.

Yet another object of the invention is to provide an apparatus for the preparation and distribution of individual dosage units of medicine prepared and distributed at different locations with a minimum of transportation of equipment therebetween.

Still another object of the invention is to provide such an apparatus which enables accurate and reliable distribution of medicines at large institutions.

Still another object of the invention is to provide such an apparatus which facilitates the preparation and organization for distribution of single dosage units of medicine prepared for distribution at different times.

Another object of the invention is to provide such an apparatus which insures security for the medicines at all times between the preparation and distribution thereof.

Yet another object of the invention is to provide such an apparatus which minimizes expense of the equipment.

BRIEF DESCRIPTION OF THE DRAWINGS

The above-mentioned and other features and objects of this invention and the manner of attaining them will become more apparent and the invention itself will be best understood by reference to the following description of an embodiment of the invention taken in conjunction with the accompanying drawings wherein:

FIG. 2 is a fragmentary perspective view of the apparatus shown with portions thereof opened to show details of the compartments and trays thereof;

FIG. 6 is a fragmentary sectional view showing construction details of the apparatus of the invention;

FIGS. 8*b*, 8*c* and 8*d* are fragmentary and perspective views of alternate constructions of the transportable module illustrated in FIGS. 4, 8 and 8*a*; and FIG. 9 is a perspective view of an alternate embodiment of the transportable module for use in the present invention.

DESCRIPTION OF A SPECIFIC EMBODIMENT

Figure 3:
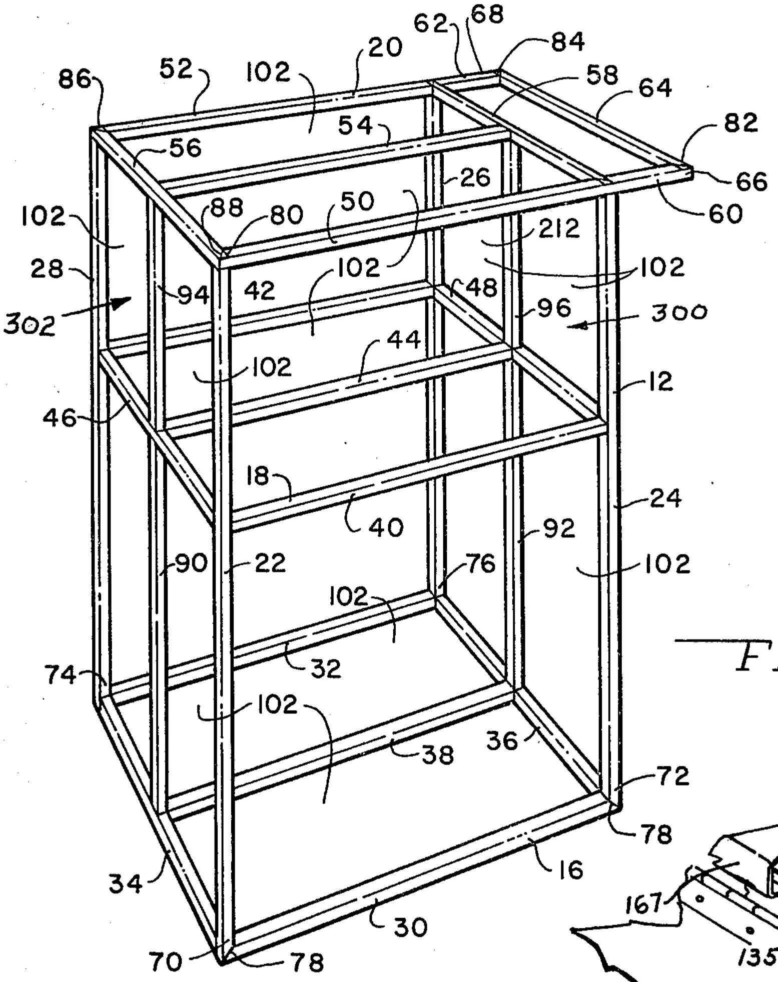
FIG. 3 is a perspective view showing details of the frame of the apparatus.

Referring now to the drawings, there is shown a single dosage pharmaceutical distribution apparatus 10 comprising a rigid frame 12 rollably supported on a plurality of wheels 14. As can best be seen in FIG. 3, frame 12 is generally rectangular and includes a base frame 16, intermediate frame 18, and upper frame 20, frames 16, 18 and 20 being supported in generally parallel, vertically spaced-apart relationship by corner members 22, 24, 26 and 28.

Bottom frame 16 is rectangular and includes front and back members 30, 32, side members 34, 36 and a central member 28 disposed parallel to and about midway between front and back members 30, 32. Members 30, 32, 34, 36 and 38 are preferably fabricated from rigid, tubular material such as aluminum having a rectangular cross-section. Middle frame 18 is similar, comprising front and back members 40, 42 and central member 44 disposed in generally parallel spaced-apart relationship and joined by side members 46, 48.

Upper frame 20 includes generally parallel, spaced-apart front and back members 50, 52, central member 54, and end members 56, 58. Preferably, members 50, 52 are longer than members 30, 40, and 32, 42 whereby they have outwardly extending end portions 60, 62, respectively. A cross member or handle 64 extends laterally between distal ends 66, 68 of members 60, 62.

Members 22, 24, 26 and 28 are preferably formed from a single piece of elongated, tubular material of rectangular cross-section to provide maximum vertical support. It will be observed that the lower ends 70, 72, 74 and 76 of members 22, 24, 26 and 28 are joined to front and back members 30, 32 of lower frame 16 with mitered joints as at 78. This method of joining the members insures that all the ends of the members such as members 30, 32 and corner members 22, 24, 26 and 28 are closed thereby preventing the accumulation of dirt and other contaminants in the interior of the tubular members of frame 12. Similarly, the corners 80, 82, 84 and 86 of top frame 20 are joined with mitered joints as at 88 to again provide closed ends for these members.

Vertical braces 90, 92, 94 and 96 extend between side frame members 34, 36, members 46, 48, and members 56, 58, respectively, at points disposed about midway between corner members 22, 28 and corner members 24, 26, respectively. It will be observed that all of the members of frame 12 are joined as described to provide closed ends to the tubular members such that contamination, dirt, or other materials cannot collect in the interiors thereof.

Wheels 14 are conventional casters and include upwardly extending pivot members (not shown) received within suitable openings (not shown) in the lower sides of members 30, 32.

Figure 1:
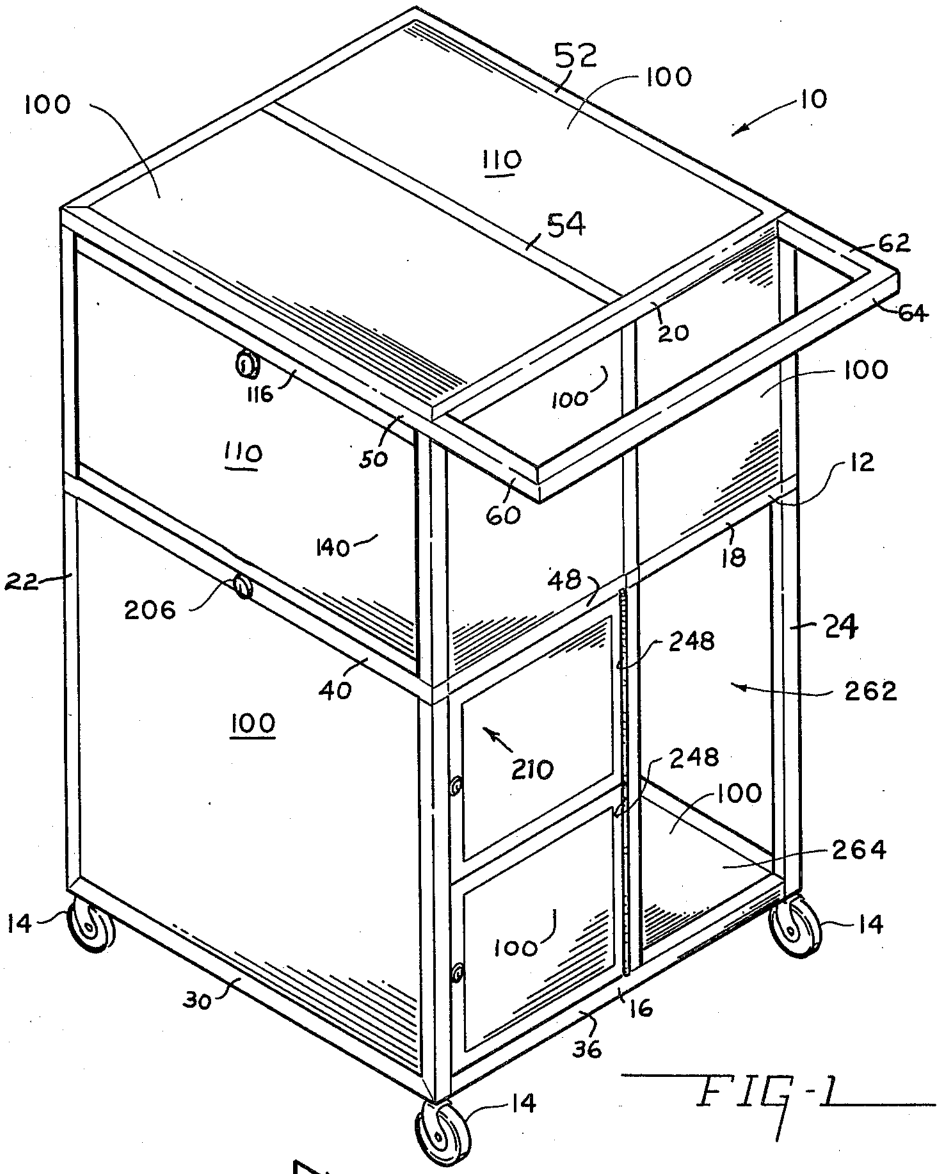
FIG. 1 is a perspective view of an apparatus in accordance with the present invention.
Figure 5:
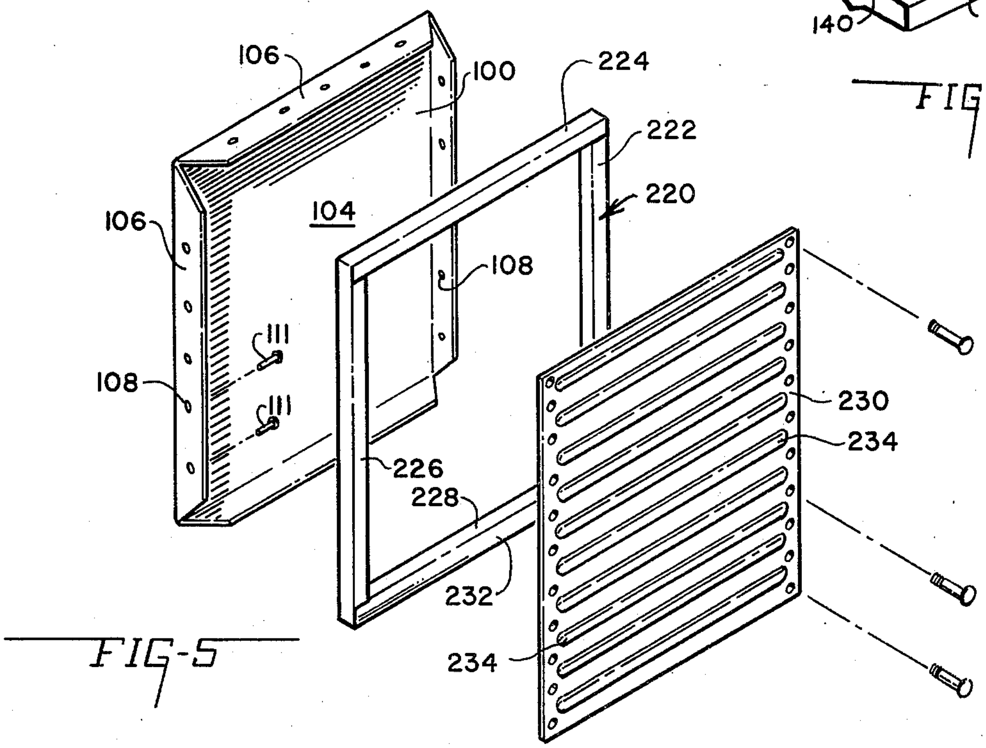
FIG. 5 is an exploded perspective view showing details of the wall construction of the apparatus of the present invention.

As best seen in FIGS. 1 and 5, a plurality of closure panels 100 are provided for closing selected ones of the openings as at 102 of frame 12. Each of panels 100 is fabricated from rigid sheet material and includes a fascia portion 104 having a plurality of inwardly turned flanges 106 extending at right angles with respect thereto. Flanges 106 are preferably formed as an integral part of the fascia portion 104 by cutting and bending the panels 100. Flanges 106 are provided with a plurality of openings as at 108 whereby the panel 100 can be secured to the inside surfaces of respective ones of the frame members with fasteners such as rivets 111. Individual ones of panels 100 are dimensioned to fit the differently sized openings 102 and it will be observed that the panels 100 are mounted with their fascia portions 104 positioned flush with the outwardly disposed surfaces of the adjacent members of the frame 12. This provides the cart with an easily cleaned and sanitized exterior surface essential in a hospital or similar type institutional environment.

Figure 4:
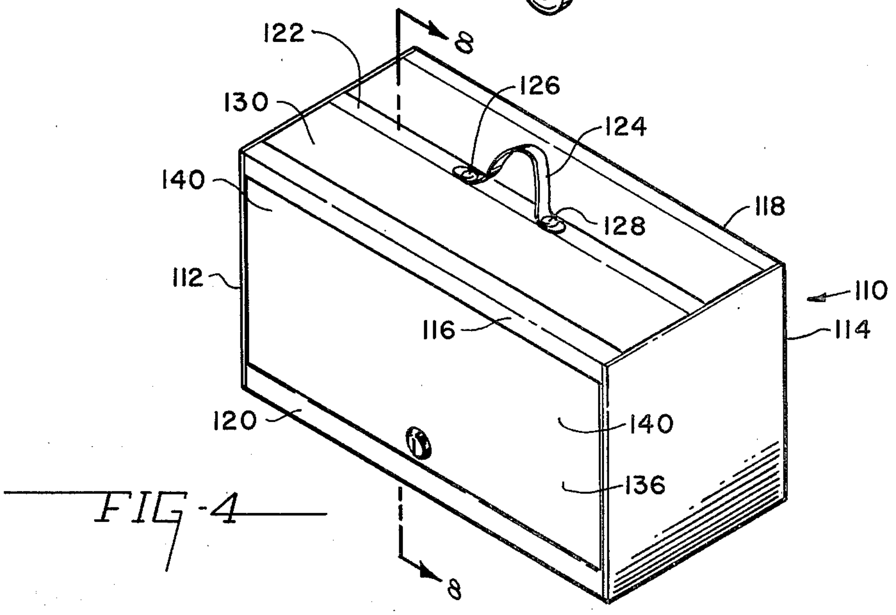
FIG. 4 is a perspective view of one of the modules which is transported between the institution and the pharmaceutical dosage preparation location.

Referring now to FIG. 4, there is illustrated a transporting case 110 for use in the present invention. Case 110 includes a pair of planar end panels 112, 114 of relatively thin yet rigid material. Panels 112, 114 are joined by four laterally extending corner posts as at 116, 118 and 120. Posts 116, 118 and 120 are again fabricated from rigid tubular material of rectangular cross-section and are joined to the panels 112, 114. A rigid brace 122 is fixedly secured between panels 112, 114 at a position generally parallel to and about midway between posts 116, 118. A carrying means such as strap 124 is secured to the brace 122 with suitable fasteners 126, 128. The top of case 110 is closed with suitable closure panels 130, 132 which may be fabricated in a manner similar to panels 100. Similarly, the back and bottom (not shown) of case 110 are closed with suitable closure panels 133, 135. The front 136 of case 110 is open and a case door 140 is secured to member 116 by means such as a hinge (described below) such that door 140 can be moved between an open and closed position. Preferably, locking means 144 is mounted to the door 140 so that the latter can be locked in its closed position to provide security for medications, drugs, and the like stored within the case 110.

Figure 8D:
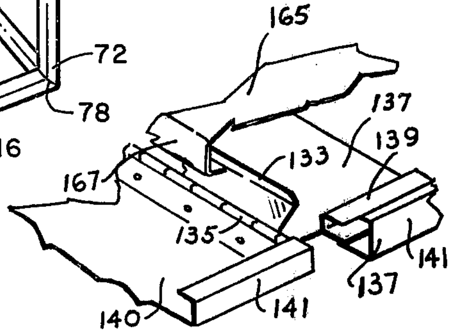
Figure 8A:
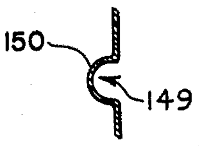
FIG. 8*a* is a fragmentary sectional view showing details of the construction of the transportable module.
Figure 8:
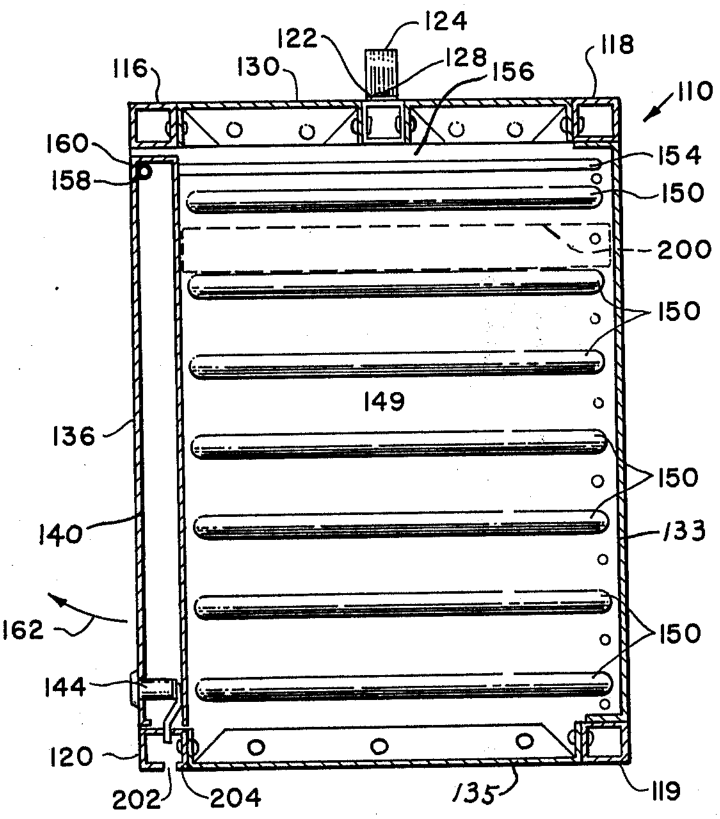
FIG. 8 is a sectional view of the transportable module taken along section line 8—8 of FIG. 4.

As can best be seen in FIG. 8, the end panels 112, 114 have secured to the inside surfaces thereof tray guide panels 149 having integrally formed thereon a plurality of tray guide tracks 150. Panels 149 are preferably fabricated from a moldable plastic with the tracks 150 being molded therein. Each of the tracks 150 has an arcuate cross-section and extends inwardly of the case 110.

Elongated slots 154 are formed in panels 149 adjacent the top edge 156 thereof. Door 140 is in turn provided with a pair of hinge pins 158 adjacent the top edge 160 thereof, pins 158 having the outwardly extending ends (not shown) thereof received in the slots 154. It will further be observed that the uppermost one of tracks 150 is disposed in parallel spaced-apart relationship to slot 154. This construction permits the door 140 to be opened as indicated by arrow 162. When the door has been moved to a generally horizontal position, the door can be slidably moved into the case 110. Thus positioned, the uppermost one of the tracks 150 will support door 140 in its open position, the door being so disposed that it will not interfere with access to the case 110, become accidentally closed, or present an obstruction that could be easily bumped by the user.

It is highly desirable that the door 140 of the transporting case 110 be hingedly connected to the case 110 such that when opened, the door 140 may be positioned out of the way to permit access to the trays (to be described hereinafter) therein without having to hold the door in an opened condition. Hereinabove, structure is disclosed whereby the door is disposed within the case 110 adjacent the top thereof. Alternately, the door 140 can be secured to the case 110 by means of a piano hinge or the like adjacent the bottom edge thereof such that the door 140 can hang from the hinge when open so as to be generally superimposed over the panels 100 closing the lower enclosure 210 of the frame 12. Alternatively, the door 140 can be hingedly connected to the transporting case 110 so as to be disposed within the case and stored adjacent the bottom thereof, as shown in FIG. 8*b*. FIG. 8*b* shows the hinge pins 158 to be secured to the door 140 adjacent its lower edge 161 and to be positioned within a channel formed by the bottom closure panel 135 and a flange member 163 spaced from but generally parallel with the panel 135.

FIG. 8*c* illustrates another construction in which a plurality of channel members 151 are secured to the end panels 112, 114 in lieu of the tray guide panels 149. These channel members have a lower flange member 153 and an upper flange member 155. Channel members 151 are secured to the end panels 112, 114 by their web portions 157 and suitable fasteners 159. It will be seen from FIG. 8*c* that flange portions 153 extend from the end panels 112, 114 a distance greater than flange portions 155; together they function to hold the trays relatively securely within the transporting case 110 while still not interfering with the contents of the trays. FIG. 8*c* also illustrates the door 140 in its storage position between the panel 135 and a false bottom 165.

FIG. 8*d* discloses still another door construction wherein bottom 165 is provided with a rolled front portion 167 and door 140 is provided with rolled peripheral portions 141 which cooperate with channel members 139 secured to the bottom 163 and positioned so as to receive portions 141 therein whenever door 140 is stored beneath the bottom 165. Door 140 is secured to door segment 137 by means of a piano hinge 135 or the like. Door segment 137 has a rolled flange portion 141 like door 140 but differs from the door portion 141 inasmuch as it never leaves channel member 139. Portion 141 of door segment 137 is maintained within the channel member 139 by means of the stop 133 which is secured to the door 140 rearwardly of the piano hinge 135 so as to engage the rolled portion 167 of the floor 165 whenever the door 140 is fully extended. Since the length of the case 110 is longer than the height of the door 140, the case 110 can receive the entire door segment 137 and door 140 therein.

Referring now to FIG. 9, there is illustrated an alternate embodiment of the transporting case 110. Case 110*a* comprises a rigid bottom panel 135*a*. Panel 135*a* is provided with a downwardly extending peripheral flange 270 and a plurality of reinforcing ribs as at 272. The upper portion of the transporting case 110*a* is formed of two like sections 274, 276. Sections 274, 276 are of generally rectangular configuration having rounded corners and are provided with overlapping flange portions as at 278. The overlapping flange portions 278 are joined by fasteners 280 and the portions 274, 276 are fixedly joined to panel 135*a* by fasteners 282. A suitable carrying handle or transporting means 284 is secured to the upper surface 286 of portions 274, 276 by fasteners (not shown) and a reinforcing plate 288. Each of sections 274 and 276 is provided with a generally perimeteral, outwardly extending groove 290, 292, respectively. Portions 274, 276 form an enclosure having an open end 294. A suitable tambour door or similar flexible panel 296 is slidably received in grooves 290, 292 for sliding movement between a first open position and a closed position closing opening 294. Preferably, door 296 is provided with a handle as at 298. The inside, side surfaces of portions 274, 276 are again provided with suitable tray guide panels 149*a* having elongated ridges 150 thereon for slidably receiving trays 166 thereon. It will be observed that the length dimension of tracks 150 is about equal to the length dimension of trays 166, trays 166 being longitudinally received in the case 110*a* rather than laterally thereinto as in case 110. Case 110*a* has the advantage of being light in weight, less expensive to produce, and yet is durable. Third locking means (not shown) may again be provided to secure the case 110*a* in frame 12.

Figure 7C:
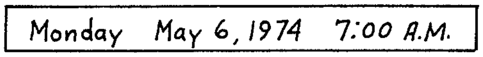
FIGS. 7*b* and 7*c* are plan views of the cards and labels used in conjunction with the dosage tray illustrated in FIG. 7 and the dosage container illustrated in FIG. 7*a;*
Figure 7:
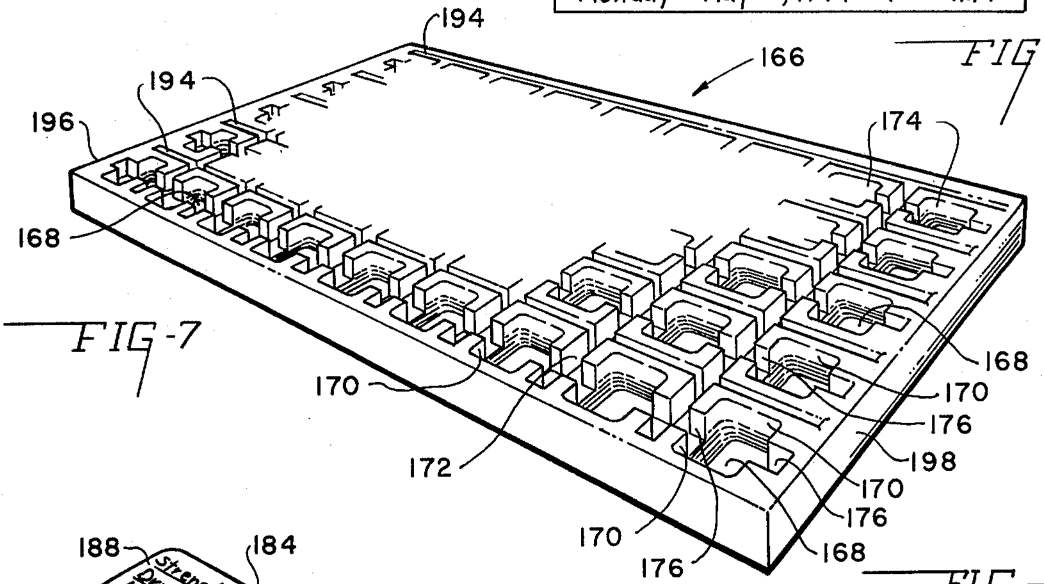
FIG. 7 is a perspective view of one of the dosage trays for use with the present invention.

Referring now to FIG. 7, there is illustrated a tray 166 used with the present invention. Tray 166 is generally rectangular in plan view and includes a multiplicity of individual pharmaceutical dosage compartments 168 (only part of which are shown for clarity). Each compartment 168 is in turn generally rectangular and bounded by wall portion 170. A slot 172 is provided between each row 174 of compartments 168. Walls 170 are further provided with notches 176 which extend therethrough in directions perpendicular to slots 172.

Figure 7A:
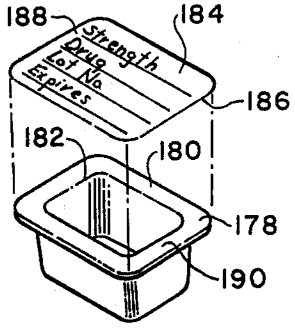
FIG. 7*a* is a perspective view of a single dosage container for use in the tray of FIG. 7.

A typical single dosage container 178 is shown in FIG. 7*a*, container 178 being a generally rectangular configuration and having a flange 180 extending outwardly from the upper perimeter 182 thereof. Container 178 is preferably molded from a suitable plastic or paper material so that it can be used once and discarded. Container 178 is further dimensioned to be snugly but removably received in compartments 168 removal thereof being facilitated by notches which provide finger access thereto.

A closure element 184 which may comprise stiff paper having a gummed under surface 186 is further provided. Closure element 184 has a peripheral configuration complementary to flange 180 and is provided with suitable indicia 188 thereon for indicating drug name, lot number, dosage, expiration date, and like information. When an individual dosage unit has been prepared at a pharmaceutical preparation center, the closure element 184 is simply adhered to the upper surface 190 of flange 180 thereby sealing the dosage therein. The individual containers 178 are then inserted into appropriate ones of the compartments 168, typically being arranged in the order of room numbers. The tray 166 can be economically fabricated from a single piece of molded plastic, the tray being rigid, durable, and easy to handle.

Figure 7B:
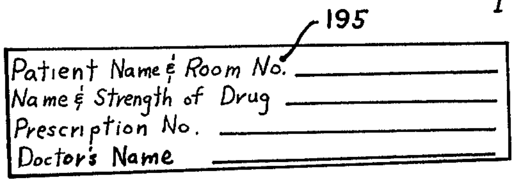

Tray 166 may further be provided with a second plurality of relatively thin slots 194 which extend longitudinally between the ends 196, 198 thereof, slots 194 being dimensioned to frictionally receive therein suitable cards 195 containing indicia identifying the patient, the prescription, the drug and the doctor pertaining to the contents of the compartments 168. See FIG. 7*b*. Each tray is marked with a date and time indicating when the drugs of the tray are to be administered; the marking is done in one embodiment by a label as shown in FIG. 7*c*.

The trays 166 are slidably received within the case 110 as indicated by dashed lines 200 in FIG. 9. When the trays have been filled and inserted within the case 110, the door 140 is closed and locked by means of the locking means 144. The individual dosage units are now secure and cannot be accidentally dislodged from the compartments, disorganized, or the like even when the cases are turned upside down. Such is true with each of the trays 166 positioned within the cases 110, 110*a* or within the enclosure 210 by providing that the distance between the guide tracks 150 of the panels 149, 149*a* and the guide tracks 234 of the panels 230, and likewise the distance between the channel members 151 be such that the distance between the trays is less than the distance between the bottom of the container 178 and the flange 180 thereof. By maintaining this dimensional relationship, the containers 178 are secure within the compartments 168 so long as the cases 110, 110*a* and the enclosure 210 have a full complement of trays or at least a tray positioned over each full or partially filled tray.

The loaded cases 110 are transported and, upon their arrival to the instution are slidably received within the upper portions of the cart 12. Preferably, members 120 of case 110 are provided with a second slot 202 in the lower surface 204 thereof, a second locking means 206 being mounted within members 40, 42 of the frame 12. When the case 110 has been inserted into the upper portions or compartment of the frame 12, locking means 206 is operated to secure the case therein.

Referring now particularly to FIGS. 1 and 2, frame 12 may further be provided with a lower enclosure 210. The top and bottom 212, 214 (FIG. 2 only) of enclosure 210 are closed with panels 100. Similarly, the sides 216, 218 thereof are closed with suitable panels 100. As best seen in FIGS. 2 and 5, tray frames 220 are fitted within the enclosure 210. Frames 220 comprise four tubular members 222, 224, 226, 228, joined into a rectangular configuration, frame 220 being dimensioned to be received within the enclosure 210 as shown in FIG. 2. Tray guide panels 230 are secured to the inside surfaces 232 of frames 220. Panels 230 are similar to panel 149 with the exception that panels 149 have tracks 150 with a length about equal to the width of the trays 166 while panels 230 have tracks 234 having the length equal to the longitudinal dimension of the trays 166 and panels 230 do not have slots such as slots 154. Trays 166 are slidably received on tracks 234 in a manner similar to the insertion thereof into the case 110. As can be seen in FIG. 2, suitable divider elements 236 can be slidably placed on the tracks 234 to divide the enclosure 210 into two or more sections.

The open end 240 of enclosure 210 is provided with a plurality of doors 242. Each door 242 includes a rectangular frame 244 fabricated from tubular members of rectangular cross-section joined by mitered joints as at 246. Closure members 100 are fitted to the frames 244 and the doors 242 are hingedly secured to the frame member 92 by means such as piano hinge 248 (FIG. 6). Preferably, the inside surface 252 of frames 244 have secured thereto panels 254. Panels 254, in combination with frames 242 and enclosure members 100, form suitable compartment 258 for receiving and storing records, charts and the like.

Doors 242 are further provided with suitable locking means 260 which cooperate with suitable slots (not shown) in frame member 24 for locking the enclosure 210. Enclosure 210 is a permanent part of the cart 12 and provides a means for receiving, organizing and distributing single dosage units of medicine of the type stocked in bulk quantities at an institution. For example, the trays 166 within the enclosure 210 can be filled with medicines such as antipyretics, analgesics, sedatives, and like medicines which are frequently supplied to patients at an institution on a demand basis. These items do not require a specific prescription and can be easily and more economically stored in bulk at the institution.

Frame 12 further includes an open compartment 262 having a floor 264 which is again an appropriately dimensioned one of panels 100. The open compartment 262 provides a convenient place to store and transport items such as soft drinks, orange juice, and other items that are frequently transported to and from individual rooms.

As can be seen in FIG. 1, the frame 12 is provided with two compartments or open spaces 300, 302 adapted to receive two cases 110 or 110*a*. The frame 12 and the cases 110 or 110*a* and the enclosures 210 are to provide security for the drugs stored therein. Thus, members, panels in facia portions of frame 12, the posts, braces, panels and doors of cases 110, 110*a* all should be fabricated of durable materials such as aluminum, steel or other metals, wood, plastic or the like, and joined together by suitable means to provide a strong and durable structure. While it may be impossible to provide ultimate security for the drugs contained therein, clearly by fabricating the aforementioned members, panels, facia portions, posts, braces and doors of such materials, entry therein without unlocking the doors thereof, will at least be obvious from the breakage or damage to the cases or enclosures whereupon an inventory of the contents can be conducted.

It will be seen that the apparatus of the present invention provides an efficient and economical means for preparing, organizing, transporting, and distributing single dosage units of pharmaceuticals and the like to patients in large institutions. The invention enables the preparation of the single dosage units at remote locations such as a pharmacy where the dosage units can be prepared with maximum efficiency. The apparatus obviates the need to store large quantities of prescription drugs at the institution thereby reducing cost and waste. The apparatus further obviates the need for hospital or institutional personnel to select, measure, and sort the dosage units at the institution thereby saving time and substantially reducing the chances of errors in the distribution of medicines.

The apparatus requires only the transport of small, portable cases. The large and relatively expensive wheeled carts of the apparatus are retained at the institution thereby reducing the cost of transportation and reducing the initial investment in such equipment since these portions of the equipment do not have to be duplicated. The apparatus provides complete security for prescription drugs and protects the same from weather and the like during transport. The apparatus in accordance with the present invention further provides convenient means for preparing, organizing and distributing quantities of demand drugs that are stored in bulk at the institution. The apparatus further provides convenient means for transporting other items such as liquids that are frequently distributed to patients along with the distribution thereto of prescribed medicines. The apparatus is relatively inexpensive to produce, is rugged, and easily maintained in a clean and sanitary condition.

While there have been described above the principles of this invention in connection with specific apparatus, it is to be clearly understood that this description is made only by way of example and not as a limitation to the scope of the invention.

What is claimed is:

1. A pharmaceutical dosage distribution apparatus comprising at least one transporting case having an opening in one side thereof, a door closing said opening and coupled to said case for movement between open and closed positions, said open position being within said case, first locking means for holding said door in said closed position, said case having a plurality of tray supports extending generally horizontally inwardly into the interior of said case, a plurality of nurse medicine pass trays adapted to be positioned on said tray supports within said case, each of said trays having a thickness dimension and a plurality of compartments therein for receiving a predetermined single dose of medication in a pre-package having a top and bottom, said tray supports being vertically spaced apart, the distance between said tray supports being less than the sum of the thickness of one of said trays and the distance between said top and bottom of one of said pre-packages, each of said trays having adjacent each of said compartments printed materials having patient and drug identification information thereon relative to the pre-package received in the adjacent compartment, a traveling nurse's station including a frame means having at least three frame compartments, a plurality of closure panels secured to said frame means enclosing at least one of said compartments, one of the remaining compartments having at least a floor, said case being slidably received in the remaining of said compartments, second locking means for locking said case to said frame means in its received position in one of said remaining compartment, said case having means thereon for manually lifting and transporting the same apart from said station, said station having a plurality of wheels operatively connected to said frame means, whereby said transporting case can be loaded at a pharmacy with said nurse medicine pass trays having said pre-packages positioned in said compartments and identified for distribution to patients at an institution at a given time, locked and transported to said institution without disloding said pre-packages from said trays, placed in said remaining compartment of one of said traveling nurse's station located at said institution, locked to said station frame means, and used during nurse's rounds.

2. The apparatus of claim 1 wherein a plurality of said pre-packages have a shape complementary to individual ones of said compartments, each of said plurality of pre-packages further including an outwardly extending peripheral flange, identifying means including a closure element adhesively secured to said peripheral flange.

3. The apparatus of claim 1 wherein said enclosed compartment is divided into two "use upon demand" medicine storage sections, both of said sections having closed top, bottom, side and back surfaces, the fronts of said sections being open, doors hingedly secured to said frame means for closing said open fronts of both of said sections, said doors being movable between open and closed positions, third locking means for locking said last mentioned doors in their closed positions.

4. The apparatus of claim 1 wherein said case further includes slot means therein extending generally horizontally thereof for securing said door to said case, said door including hinge means slidably received in said slots for hingedly connecting said door to said case, whereby said door can be pivoted to extend laterally outwardly therefrom and can be slidably moved into said transporting case, means for supporting said door within said case.

5. A pharmaceutical dosage distribution apparatus comprising at least one transporting case having an opening in one side thereof, a door closing said opening and coupled to said case for movement between open and closed positions, said open position being within said case, first locking means for holding said door in said closed position, said case having a plurality of tray supports extending generally horizontally inwardly into the interior of said case, a plurality of nurse medicine pass trays adapted to be positioned on said tray supports within said case, each of said trays having a plurality of compartments therein for receiving pre-packages of medication, said tray supports being vertically spaced apart, each of said trays having adjacent each of said compartments printed materials having patient and drug identification information thereon relative to the pre-package received in the adjacent compartment, said trays when positioned on said tray supports are spaced apart but in close proximity to adjacent trays, whereby the overlaying adjacent tray maintains each pre-package of each tray in its own compartment, second locking means for locking said case to a traveling nurse's station, and means for manually lifting and transporting said case apart from said station, whereby said transporting case can be loaded at a pharmacy with said nurse medicine pass trays having said pre-packages positioned in said compartments and identified for distribution to patients at an institution at a given time, locked and transported to said institution without dislodging said pre-packages from said trays, placed in and locked to a traveling nurse's station at said institution, and used during nurse's rounds.

6. A pharmaceutical dosage distribution apparatus comprising at least one transporting case having an opening in one side thereof, a door closing said opening and coupled to said case for movement between open and closed positions, said open position being within said case, first locking means for holding said door in said closed position, said case having a plurality of tray supports extending generally horizontally inwardly into the interior of said case for supporting thereon in a vertically spaced apart relation but in close proximity to adjacent trays a plurality of nurse medicine pass trays having a plurality of compartments therein for receiving pre-packages of medication, whereby the overlaying adjacent try maintains each pre-package of each tray in its own compartment, second locking means for locking said case to a traveling nurse's station, and means for manually lifting and transporting said case apart from said station, whereby said transporting case can be loaded at a pharmacy with said nurse medicine pass trays having said pre-packages positioned in said compartments and identified for distribution to patients at an institution at a given time, locked and transported to said institution without dislodging said pre-packages from said trays, placed in and locked to a traveling nurse's station at an institution, and used during nurse's rounds.

* * * * *